United States Patent [19]

Ratkoff et al.

[11] Patent Number: 4,944,297
[45] Date of Patent: Jul. 31, 1990

[54] PORTABLE APPARATUS FOR LOCALIZED HEATING OF THE SKIN FOR THERAPEUTIC PURPOSES

[76] Inventors: Georges Ratkoff, 7 chemin de la Guinguette La Taye, 28120 Illiers Combray; Jean-Paul Deheuvels, 12 rue de Beauce Barjouville, 28630 Chartres, both of France

[21] Appl. No.: 249,759

[22] Filed: Sep. 27, 1988

[30] Foreign Application Priority Data

Oct. 7, 1987 [FR] France .................. 87 13825

[51] Int. Cl.$^5$ ............................................. A61F 7/00
[52] U.S. Cl. ........................................ 128/399; 128/396
[58] Field of Search ............... 128/23, 24.1, 395, 396, 128/399; 219/552; 362/171

[56] References Cited

U.S. PATENT DOCUMENTS

| | | | |
|---|---|---|---|
| 861,019 | 7/1907 | Coger | 128/396 |
| 1,415,784 | 5/1922 | Brock . | |
| 1,502,251 | 7/1924 | Kanazawa . | |
| 2,533,955 | 12/1950 | Pitts | 128/396 |
| 2,538,685 | 1/1951 | Hansen et al. | 128/396 |
| 2,906,264 | 1/1958 | Jefferson . | |
| 3,946,733 | 3/1976 | Han . | |
| 4,261,364 | 4/1981 | Haddad et al. . | |
| 4,381,009 | 4/1983 | Del Bon . | |
| 4,622,972 | 11/1986 | Giebeler . | |
| 4,658,823 | 4/1987 | Beddoe et al. . | |

Primary Examiner—Edward M. Coven
Assistant Examiner—Mark S. Graham
Attorney, Agent, or Firm—Griffin, Branigan & Butler

[57] ABSTRACT

The apparatus has an elongated body (6) having an open end (7) in a plane (8) which is pressed against the surface (2A) of the skin (2) around a location that has been stung by a sting (1) which has caused venom to diffuse (5) in the skin. The end is pressed in such a manner as to enable a heater element (9) set back from the opening (7) to apply a heat flux to the skin lying in the range 0.03 W/mm$^2$ and 0.30 W/mm$^2$ such that the penetration (2B) of the heat into the skin heats up the skin to between 50° C. and 60°0 C., thereby destroying the venom.

12 Claims, 2 Drawing Sheets

PORTABLE APPARATUS FOR LOCALIZED HEATING OF THE SKIN FOR THERAPEUTIC PURPOSES

BACKGROUND OF THE INVENTION

The invention relates to a portable apparatus for localized heating of the skin and intended mainly for therapeutic use, in particular for suppressing the disagreeable and even painful effects caused by the stings and bites of insects such as the hymenoptera (bees, wasps, hornets, ants, . . . ) and sea creatures such as weavers or sting fish, scorpion fish, jelly fish etc . . .

The venom of these creatures is destroyed by heat. An old known method consists in strongly heating the region attacked by a sting or bite by bringing the stung or bitten location close to a lighted cigarette or a hot object such as an iron heated to red heat.

This method is difficult to apply; it is incapable of heating the skin at exactly the desired location to the minimum temperature required and for a sufficient period of time to guarantee destroying the venom while avoiding running the risk of burning the skin.

At present there exists no small lightweight apparatus which is easily carried on the person and easily operated under all circumstances for providing localized heating of a region of the skin which has been bitten or stung by an insect or a sea creature having a thermolabile venom.

The main object of the invention is therefore to provide such a heating apparatus having the above-mentioned advantages and qualities.

It should be naturally understood that the use of apparatus of the invention is not limited to treating zones which have been stung or bitten and that the apparatus can be used wherever there is a need for localized heating of the skin for whatever reason.

Apparatuses are already known for the purpose of obtaining localized heating of the skin, as described, for example, in the following patent documents No. FR-A-1 139 096, U.S. Pat. Nos. 4,505,545, and 4,658,823.

Each of the apparatuses described in these three documents comprises a hollow elongate body having an open end, an electric lightbulb mounted in said body in the vicinity of its opposite end which is closed, and a reflector placed behind the lightbulb close to the closed end of the body. These apparatuses are used by putting the closed end into contact with the skin or in the vicinity of the skin while the lightbulb is powered with electricity and serves as a source of heat.

However, these three apparatuses are designed to be powered directly from the mains; the power specified for the bulbs is at least 15 W to 25 W and may be as much as several hundred watts. These apparatuses therefore cannot be carried on the person and cannot be powered from batteries or rechargeable batteries which are small enough to be easily transported. Further, the heat flux produced is not accurately determined. They are intended to heat the skin to a temperature which is not specified. The apparatus of above-mentioned U.S. Pat. No. 4,658,823 includes a thermostat but the thermostat is provided solely as a cut-off means for use when it is in danger of reaching a high limiting temperature value which could be dangerous for the user. This apparatus is intended for heating an ear as a whole, and it also includes openings of adjustable section to admit cold outside air without monitoring the temperature.

Temperature sensitive venoms are destroyed, depending on circumstances at temperatures lying between 50° C. and 60° C., which temperatures must be applied for a period of time lying between 20 seconds to 30 seconds for hymenoptera and between 1 minute to 3 minutes for sea creatures. Further, the venom begins to diffuse in the tissue immediately after it has been stung or bitten and it is desirable for the effective temperature to be applied to the skin without loss of time. In practice, once the apparatus has been put into place against the skin and has begun to heat the skin, it is desirable for the effective temperature of 50° C. to 60° C., to be reached in less than 1 minute.

If account is taken of the fact that the value of 60° C. lies at the beginning of the temperature zone which the skin can withstand for a few moments only prior to starting to burn, it is quite clear that prior apparatuses do not have the characteristics which enable them to treat bites and stings reliably without burning the skin.

It may be observed that using a thermostat for the purpose of avoiding the danger of burning nevertheless suffers from the drawback of increasing the weight and the price of the apparatus. In order to ensure that the apparatus is portable and widely available, it is necessary to ensure, in addition, that it is as lightweight and as cheap as possible.

SUMMARY

Apparatus suitable for localized heating of the skin for therapeutic purposes, in particular for destroying venom injected into the skin by the sting or the bite or certain insects and sea creatures, the apparatus comprising a hollow elongate body having an open end, a source of heat flux mounted in the hollow body and set back from said open end, a reflector placed in said body behind said source relative to the open end, and an energy supply source received in the body and connected to the heat flux source in a manner which is interruptible at will, is characterized in accordance with the invention in that the ratio between the power of the heat flux source and the free area of the open end lies in the range 0.03 W/mm$^2$ and 0.30 W/mm$^2$, and preferably in the range 0.04 W/mm$^2$ and 0.25 W/mm$^2$.

When the apparatus of the invention is used, the open end of the apparatus is pressed against the skin such that the above-mentioned power per unit area is actually applied to the skin in a region containing the precise location of the bite or sting, which location should preferably be in the center of said zone.

This power density may be obtained by means of numerous different sources of heat flux; and in the context of the invention the source should have a power rating lying in the range 0.8 W to 3 W.

As described below, an electrical resistance fed from an electric battery or a rechargeable battery serving as a source of energy, may be suitable. However, it is preferable to adopt an electric lightbulb as the source of flux, said bulb developing power lying in the range 0.12 W/mm$^2$ to 0.20 W/mm$^2$, with the area being the section area of the bulb on a plane parallel to the plane containing the open end of the body of the apparatus, and the distance between said plane containing the open end and the closest point of the bulb to said plane being about 2 mm.

In a preferred embodiment, the electric lightbulb used has a power of about 1.25 W and an outside diameter measured in a plane parallel to the plane of the open end of about 3 mm such that it develops a power of 0.17 W/mm$^2$; the free area of the open end is about 28 mm$^2$ and it is situated at a distance of about 2 mm from the closest point of the lightbulb; advantageously, the electric bulb has a nominal voltage of about 5 V and the source of energy from which it is powered has a nominal voltage of about 9 V.

Several embodiments of a portable apparatus for localized heating of the skin for the purpose of destroying venom injected by the sting or bite of an insect or of a sea creature are described for the purpose of making the invention well understood. Reference is made to the accompanying drawings, in which:

DESCRIPTIONS OF THE PREFERRED EMBODIMENTS

Figure 1:
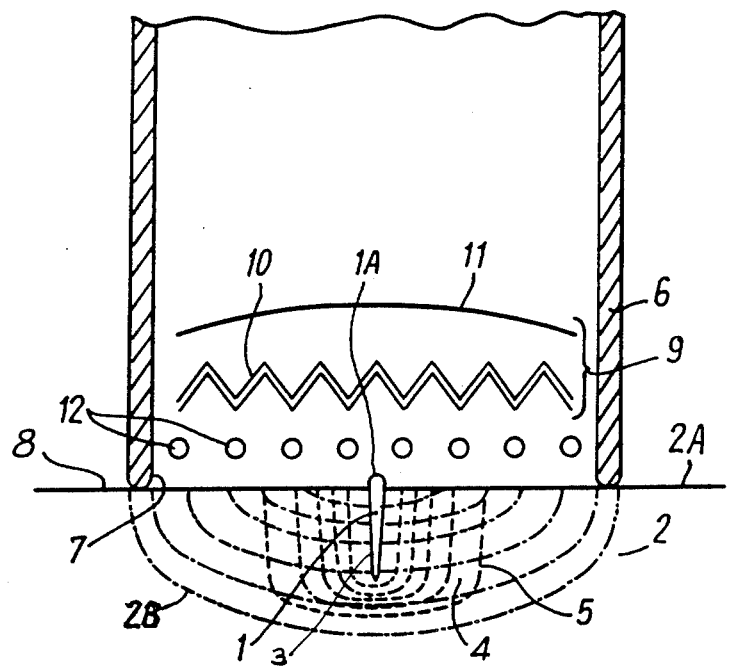
FIG. 1 is a fragmentary section view through an apparatus in accordance with the invention while being used on the skin at a location which has been stung.
Figure 2:
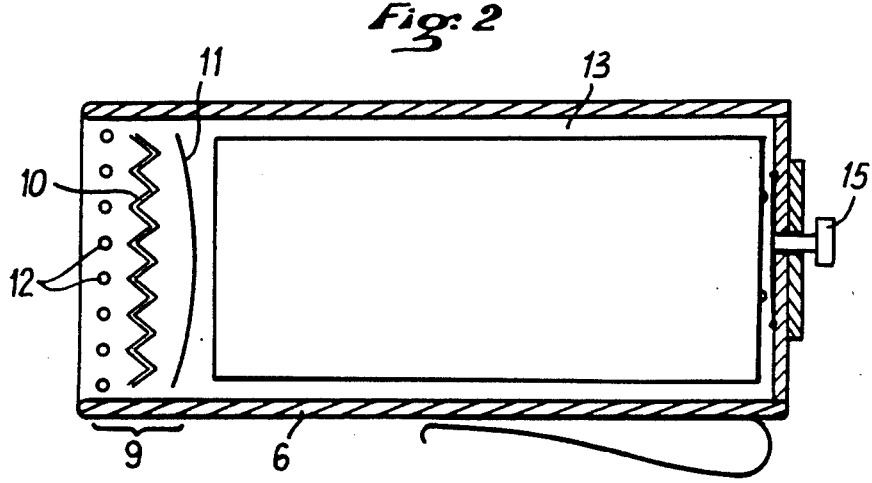
FIG. 2 is a diagrammatic section through the entire FIG. 1 apparatus.

FIG. 1 also serves to explain the effect of a string, e.g. a bee sting, when a sting 1 has penetrated into the skin 2 of a subject. In general, the external portion 3 of the sting 1 is coated with a venom which spreads by diffusion in the region 4 of the skin 2 surrounding the stung location. The diffusion of the venom is represented by a set of dashed lines 5 at progressively greater distances from the sting 1. There is often a portion 1A of the sting which projects above the surface 2A of the skin 2.

FIG. 1 shows a section of a portion of apparatus in accordance with the invention pressed against the skin 2 around the sting 1 or the location that has been stung. The apparatus has an elongate hollow body 6 with an open end 7 contained in a plane 8. The heater element 9 is fixed inside the body 6 so as to be set back slightly from the plane 8 at the open end 7.

The heater element 9 is capable of emitting heat flux to the outside of the body 6 through the open end 7. It is advantageously constituted by an electrical resistance which is associated with a reflector 11 placed inside the body 6 behind said resistance relative to the open end 7.

The set-back position of the heater element 9 relative to the plane 8 of the open end 7 has the purpose both of avoiding pressing the sting 1 into the skin, if still present therein, and also of making direct contact between the heater element 9 and the skin impossible. A distance of about 2 mm between the plane 8 of the open end 7 and the point of the heater element 9 closest to said plane is satisfactory when the ratio between the power of the heater element 9 and the area of the open end 7 lies between 0.03 W/mm$^2$ and 0.30 W/mm$^2$, as mentioned above. The difference between these two extreme values is essentially manifested by a difference in the speed with which the skin heats up. However it is preferable to adopt a ratio lying between 0.04 W/mm$^2$ and 0.25 W/mm$^2$.

The apparatus of the invention is used by applying the plane 8 containing the open end 7 against the surface 2A of the skin 2 and by switching on the heater element 9. The heating radiation emitted by the element passes through the volume of air existing between said element 9 and the surface 2A of the skin 2, and penetrates progressively into the skin as indicated in FIG. 1 by a set of dot-dashed lines 2B. The heat penetrates into the skin and affects the entire volume containing the venom. The venom is destroyed when said volume is raised to the above-mentioned temperature for the specified length of time.

In practice, the open end 7 is advantageously circular and should not be too small in diameter so as to facilitate surrounding the sting 1. However it should not be too large in diameter so as to avoid heating an excessive volume. It has been observed that an optimum value for the diameter of the open end 7 in the plane 8 is 6 mm, giving an area of 28 mm$^2$. Such an area makes it possible to achieve an above-defined ratio value by using a heater element having a fairly moderate power rating of about 1.25 W, thereby making it possible to provide a self-contained portable apparatus capable of operating for a period of time which is long enough to be acceptable in practice.

It is possible, if judged desirable, to place a protective grid 12 in the body 6 between the plane 8 of the open end 7 and the heater element 9 This grid provides both mechanical protection for the heater element and also positively prevents any direct contact therewith. In a variant (not shown) the grid 12 may be replaced by a solid wall which is transparent to the heat flux emitted by the heater element.

When the apparatus satisfies the above-mentioned general conditions, it performs its function effectively; however, it will be understood that in order to make an apparatus which is as cheap as possible, the realization of the heater element is of major importance.

In the prior documents discussed above, the heater element is an electric lightbulb. Mass-produced, cheaply manufactured heater elements of this type are commercially available. There therefore follows a description with reference to FIGS. 3 to 5 of a preferred embodiment of the invention using an electric lightbulb. However, as shown below, choosing an appropriate lightbulb is not as easy as it might appear.

Figure 3:
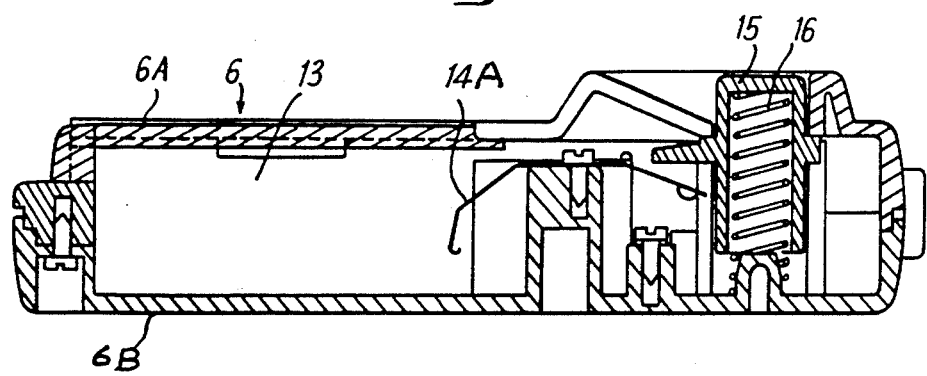
FIG. 3 is a section view on a longitudinal plane through a preferred embodiment in accordance with the invention.
Figure 4:
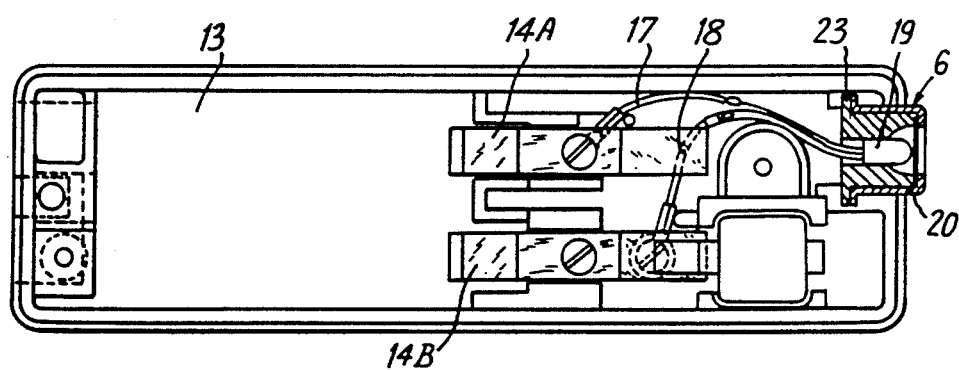
FIG. 4 is a section view on a longitudinal plane through the FIG. 3 apparatus, with the section plane being perpendicular to the section plane of FIG. 3.

FIG. 3 shows that the elongate hollow body 6 of the apparatus is made in two halves 6A and 6B which are assembled to each other in a mid-plane. In a first portion in the longitudinal direction of the hollow body volume, there is a housing 13 for receiving a source of electricity (battery or rechargeable battery) and including two flexible blades 14A and 14B for making contact with the terminals of said source. The blades 14A and 14B extend into the second portion in the longitudinal direction of the hollow body 6, which portion includes a pushbutton 15 associated with a return spring 16 for switching on and off the circuit which is connected to the flexible blades 14A and 14B. In addition to the pushbutton 15, this circuit includes two conductors 17 and 18 leading to a bulb 19 (FIG. 4). The bulb 19 is mounted so as to be set back from an open end portion 7 of the body 6.

The end portion 7 projects from the end face of the body 6. It is constituted by a cup 20 (more clearly visible in FIG. 5) which has a 6 mm diameter opening 21 at one end and which has a flange 22 at its opposite end. Two opposing halfrecesses are provided in the two halves 6A and 6B of the body 6 including grooves 23 such that a large portion of the cup 20 can be received in the half-recesses with its flange 22 being engaged in the grooves 23.

The cup 20 (FIG. 5) contains a reflector 24 which is a solid body having a longitudinal central hole 25 with a diameter of 3 mm for containing a cylindrical electrical lightbulb 19 as a push fit. The hole 25 opens out into an open recess having a substantially reflecting surface 26 formed in the portion of the reflector 24 which is closest to the opening 21 such that the filament of the bulb 19 lies at the focus of the surface 26. The reflector 24 is also provided with a flange 28 which presses against the flange 22 of the cup 20 when the reflector 24 is in place in the cup 20. After being mounted in the body 6, the two flanges 22 and 28 are contained in the grooves 23 of the two halves 6A and 6B.

Figure 5:
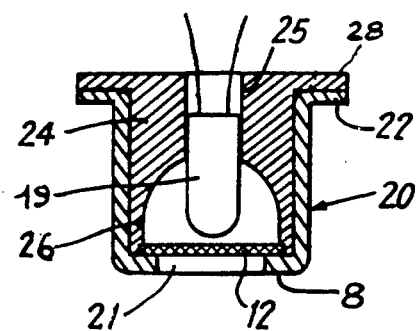
FIG. 5 is a view on a larger scale of a detail showing how the neat flux source is mounted in said apparatus.

It is also possible to provide a protective grid 12 as shown in FIG. 5, with the grid being clamped between the end face of the reflector 24 pressing against the inside face of the end wall in which the opening 21 is formed.

The bulb 19 is commercially available. It has a nominal feed voltage of about 5 V, but the source of energy to be placed in the housing 13 should have a nominal voltage of 9 V. The bulb is thus overdriven when in use and develops a power of about 1.25 W. Since it has a diameter of 3 mm, its cross-section is about 7 mm$^2$ in area and it therefore provides about 0.17 W per mm$^2$ of its cross-section (0.17 W/mm$^2$). This cross-section lies in a plane parallel to the plane of the opening 21.

The bulb 19 is commercially available under the references OR 715×5 V 115 mA×T1 3.17 X 6.35. Other bulbs may be satisfactory, but it is important for the feed voltage to be at least 50% greater than the nominal voltage. In the present example, the feed voltage (9 V) is 80% greater than the nominal voltage of the bulb. Naturally, the greater the extent to which the bulb is overdriven, the shorter its lifetime. Overdriving by 100% gives rise to almost immediate destruction of the bulb filament. Overdriving at between 50% and 90%, and preferably at 80%, is more advantageous.

While the above-described apparatus is in use, the outside end face 8 of the cup 20 is pressed against the skin. The distance between the plane of said end face 8 and the closest point of the bulb 19 is about 2 mm. This distance is easily modified and adjusted (as may be necessary when the electric voltage provided by the power supply begins to drop) by virtue of the bulb 19 being a push fit in the reflector 24.

The grid 12 is constituted, for example, by a metal sheet made of woven brass wire having a diameter of 0.30 mm and having a mesh size of about 500 microns, giving an empty fraction of about 40%.

At least the cup 20 and the reflector 24 and preferably the entire elongate body 6 are made of a substance which is a poor conductor of heat.

It is possible to omit the reflector 11 or the reflecting surface 26, but that does not provide any particular advantage, indeed the power emitted by the bulb towards the skin is reduced thereby, such that the time during which the skin needs heating is increased.

We claim:

1. Apparatus for localized heating of the skin for therapeutic purposes, in particular for destroying venom injected into the skin by the sting or bite of certain insects and sea creatures, the apparatus comprising:
a hollow elongated body having an open end, a source of heat flux mounted in the hollow body and set back from said open end, a reflector placed in said body behind said source relative to the open end for directing energy radiating from said source to said open end, and an energy supply source contained in the body and connected to the heat flux source in a manner which is interruptible at will, wherein the heat flux source has a predetermined power output and the open end has a predetermined free area such that the ratio between the power of the heat flux source and the free area of the open end lies in the range 0.03 W/mm$^2$ and 0.30 W/mm$^2$.

2. Apparatus according to claim 1 wherein the heat flux source has a power output lying in the range of 0.8 W and 3 W.

3. Apparatus according to claim 1 wherein the heat flux source is an electric light bulb, said bulb developing a power density lying in the range 0.12 W/mm$^2$ to 0.20 W/mm$^2$, with the are being the area of the cross-section of said bulb on a plane parallel to the plane containing the open end of the body of the apparatus, and the distance between said plane containing the open end and the point of the bulb closest to said plane being about 2 mm.

4. Apparatus according to claim 3 wherein said power density developed by the bulb is about 0.17 W/mm$^2$.

5. Apparatus according to claim 1 wherein the source of heat flux is an electric bulb having a power of about 1.25 W and an outside diameter in a plane parallel to the plane containing the open end of the body of about 3 mm.

6. Apparatus according to claim 1 wherein the source of heat flux is an electric bulb having a power of about 1.25 W and an outside diameter in a plane parallel to the plane containing the open end of the body of about 3 mm.

7. Apparatus according to claim 6 wherein the free area of the open end of the body is about 28 mm$^2$ and is situated at a distance of about 2 mm from the closest point of the bulb.

8. Apparatus according to claim 3 further comprising an electric energy supply source wherein the bulb is fed from said electric energy supply source said supply source having a voltage which is 50% to 90% greater than the nominal voltage of said bulb.

9. Apparatus according to claim 8 wherein the electric bulb has a nominal voltage of about 5 V and the energy supply source is an electric battery or rechargeable battery having a nominal output voltage of about 9 V.

10. Apparatus according to claim 8 wherein the bulb is cylindrical and is push fitted into a hole provided in the reflector, the reflector having an open recess with a reflecting surface into which the hole opens out.

11. Apparatus according to claim 1 wherein the predetermined power output of the flux source and the free area of the open end are fixed.

12. Apparatus according to claim 1 wherein the ratio between the power of the heat flux source and the free area of the open end is about 0.03 W/mm$^2$.

* * * * *